United States Patent [19]

Larimore

[11] 4,112,941
[45] Sep. 12, 1978

[54] ELECTRODE AND MAGNETIC CONNECTOR ASSEMBLY

[75] Inventor: Frank C. Larimore, Shoreview, Minn.

[73] Assignee: Minnesota Mining and Manufacturing Company, St. Paul, Minn.

[21] Appl. No.: 757,148

[22] Filed: Jan. 6, 1977

[51] Int. Cl.² .............................................. A61B 5/04
[52] U.S. Cl. ............................ 128/2.06 E; 128/2.1 E; 128/417; 128/DIG. 4; 339/12 R; 339/45 R; 339/46
[58] Field of Search ............... 128/2.06 E, 2.1 E, 404, 128/410, 411, 416, 417, 418, DIG. 4; 339/12 R, 12 G, 12 V, 45 R, 46

[56] References Cited

U.S. PATENT DOCUMENTS

| 3,752,151 | 8/1973 | Robichaud | 128/2.06 E |
|---|---|---|---|
| 3,805,769 | 4/1974 | Sessions | 128/2.06 E |
| 3,808,577 | 4/1974 | Mathauser | 339/12 R |
| 3,810,258 | 5/1974 | Mathauser | 339/12 R |
| 3,841,312 | 10/1974 | Corasanti | 128/2.06 E |
| 3,964,470 | 6/1976 | Trombley | 128/2.1 E |
| 4,004,298 | 1/1977 | Freed | 339/12 G |
| 4,025,964 | 5/1977 | Owens | 339/12 R |
| 4,067,342 | 1/1978 | Burton | 128/418 |

FOREIGN PATENT DOCUMENTS 1,051,180   1/1954   France ................................... 339/12 G Primary Examiner—Lee S. Cohen
Attorney, Agent, or Firm—Cruzan Alexander; Donald M. Sell; Carolyn A. Bates

[57] ABSTRACT

An improved biomedical electrode and connector assembly is disclosed wherein the connector contains a magnet to facilitate mating with an elongated upstanding contact member of the electrode. Electrical contact between the connector and the electrode occurs along some portion of the upstanding contact member so that a space or gap is formed between the connector and the electrode plate of the electrode. Apparatus whereby the connector may be intentionally disconnected with ease, but accidental disconnection is prevented, are also provided.

7 Claims, 8 Drawing Figures

ELECTRODE AND MAGNETIC CONNECTOR ASSEMBLY

The present invention relates generally to medical electrodes and connectors for effecting an electrical connection between the skin of a patient and electromedical devices such as electrocardiographs and the like. More particularly, it relates to an improved electrode-connector assembly utilizing magnetic means to effect connection.

In recent years a variety of disposable skin electrodes have been introduced into the medical field. Generally, these electrodes are adhesively secured to the skin of the patient and contain a male terminal or "stud" which is adapted to snap into a female terminal in the connector. A lead wire attached to the female terminal completes the electrical connection between the male terminal and the electromedical device. The stud portion of the electrode is generally connected to a metallic plate which is in turn connected to the skin by means of an electrically conductive material such as an electrolyte gel.

The major disadvantage associated with these "snap on" connectors is that a relatively large amount of downward force is required to mate the male portion of the electrode with the female portion of the connector. If the mating is accomplished after the electrode has been secured to the skin of a patient, the downward force often results in a spreading of the electrolyte gel. Spreading of the gel may adversely affect the electrical connection to the skin, shorten the useful life (application time) and also interfere with and weaken the adhesive which holds the electrode on the skin. A further problem involves discomfort to the patient resulting from applying pressure to a sensitive area of the body. Therefore, it has generally been necessary to mate the electrode and connector prior to securing the electrode to the skin. This method is more cumbersome and less efficient.

The problem associated with snap on connector described above has been somewhat alleviated by the use of a clamp connector such as that described in U.S. Pat. No. 3,840,703. This clamp connector has a "clothespin" design, and the user squeezes on the arms of the connector until the opening is large enough to fit around the male portion of the electrode. No downward pressure is required. However, this type of connector can in certain situations be disconnected from the electrode by accidental bumping or by applying tension on the lead wire. It is not well suited for long term monitoring of patients who enjoy freedom of movement.

By utilizing magnetic means to effect connection between the electrode and the connector, the present invention overcomes a major disadvantage associated with prior art skin electrodes and connectors. By using magnetic force to mate the male portion of the electrode with the female portion of the connector, no downward force on the electrode is required.

The use of magnetic means to effect electrical contact is known. U.S. Pat. No. 3,810,258 describes a quick connect electrical coupler comprising a male coupling half and a female coupling half. Each half contains electrical contact means and a permanent magnet. A conical projection in the male half mates with a matching recess in the female half to insure easy alignment when the two halves are assembled.

U.S. Pat. No. 3,964,470 describes a percutaneous intradermal electrical connection system and implant device. The lower portion of the implant device is located beneath the surface of the skin. The upper portion of the implant device contains a cavity which receives an extension of the connector to provide mechanical and electrical contact between the implant device and the connector. In one embodiment, the connection is achieved by magnetic means.

SUMMARY OF THE INVENTION

The present invention provides an improved skin electrode and connector assembly. The electrode portion of the assembly comprises a ferromagnetic electrode plate and an upstanding contact member firmly affixed to the electrode plate, some portion of which forms an electrical contact surface with the connector. Means are provided to adhesively attach the electrode plate to the surface of the skin in a manner that provides secure attachment and good electrical coupling for conducting electrical impulses between the skin and the electrode plate.

The connector portion of the assembly comprises a magnet having a hole in its lower surface for mating with the upstanding contact member, and a lead wire electrically connected to the magnet. The hole in the lower surface of the magnet is formed so that, when mated with the upstanding contact member of the electrode, electrical contact between the electrode and the connector is made on some portion of the upstanding contact member, and a small space is provided between the lower surface of the connector and the top surface of the electrode plate.

The term "ferromagnetic" as used herein refers to any magnetically-responsive material.

The electrode-connector assembly of the present invention provides numerous advantages over those of the prior art. Since the connection between the electrode and the connector is accomplished by magnetic means, no downward pressure on the electrode is required to mate the connector with the electrode, and the connection can be conveniently made after the electrode is in place on the patient's skin.

The mating parts are automatically aligned with the upstanding contact member enters the mating hole in the connector. When mated, the upstanding contact member prevents lateral displacement of the connector and thereby minimizes the possibility of accidental disconnection by tension on the lead wire. Since the connector can be rotated through a 360° angle about the contact member, torsional forces on the lead wire do not interfere with the electrical connection and the patient enjoys greater freedom of movement.

The major improvement in the electrode-connector assembly of the present invention resides in the mating arrangement between the connector and the electrode. The upstanding contact member of the electrode and the mating hole of the connector are designed so that, when mated, contact between the connector and the electrode occurs on some portion of the upstanding member and not on the surface of the electrode plate. The surface of the electrode plate is separated from the lower portion of the connector by a small space. In this manner, electrical contact between the mating parts is improved because the contact pressure is concentrated over a small surface area. There is less chance of dust and debris collecting on the contact surface to interfere with electrical contact. Additionally, the existence of a small air space between the connector and the electrode plate allows the electrode to be more efficiently and economically constructed. The entire top surface of the electrode plate (except for a hole to accommodate the upstanding contact member) can be covered with an adhesive strip for attaching the electrode to the skin.

The most preferred embodiment of the invention provides an additional improvement over magnetic connectors of the prior art. In this embodiment, the upstanding contact member of the electrode comprises an elongated cylindrical member or "pin." The mating hole of the connector is formed so that when the pin and hole are mated there is sufficient clearance between the pin and the wall of the hole to allow the connector to be tilted and lifted off the pin by upward force on the edge of the connector opposite the lead wire, but insufficient clearance to allow the connector to be lifted off the pin by upward force on the lead wire. Upward force on the lead wire causes the pin to intercept the wall of the hole and prevent disconnection. In this embodiment, lifting means are provided on the edge of the connector opposite the lead wire.

This improvement allows easy disconnection of the connector from the electrode by breaking the magnetic force field at one edge. In this manner, considerably less force is required than if disconnection is made by straight axial pull across the full magnetic field. Thus, intentional disconnection is facilitated, but accidental disconnection by upward force on the lead wire is prevented. Although it is most preferred to practice this improvement together with the improvement wherein electrical contact between the connector and the electrode occurs on some portion of the upstanding contact member, these improvements may be practiced separately.

DESCRIPTION OF THE DRAWINGS

Understanding of the invention will be facilitated by reference to the accompanying drawings wherein.

DETAILED DESCRIPTION OF THE INVENTION

Figure 1:
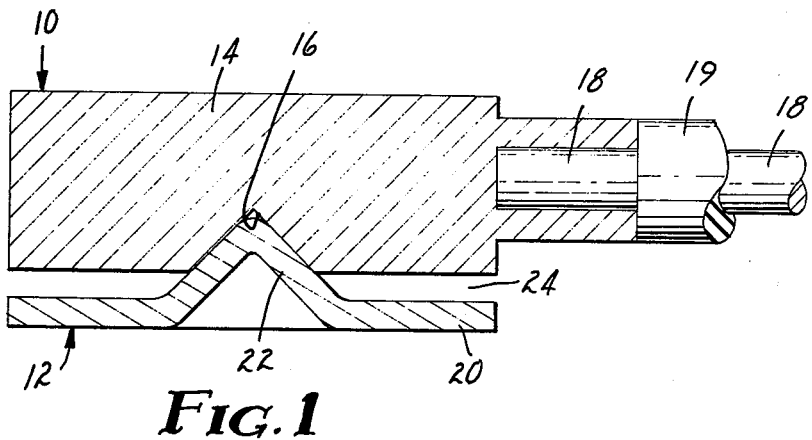
FIG. 1 is a sectional view of the connector portion of the assembly and the upper portion of the electrode.

In FIG. 1 connector 10 is magnetically and electrically connected to electrode 12. Connector 10 comprises a magnet 14 having a hole 16 in the lower surface thereof for mating with projecting portion of the electrode and a lead wire 18 electrically connected to the magnet. Lead wire 18 is encased in a protective sheath 19 and connects to an electrocardiograph or the like in the conventional manner.

The electrode 12 of the assembly shown in FIG. 1 comprises an electrode plate 20 of ferromagnetic material and an upstanding contact member 22 firmly affixed thereto. In this embodiment, the upstanding contact member 22 is a cone-shaped projection. The diameter of mating hole 16 at its opening is smaller than the diameter of upstanding contact member 22 at its base. Consequently, when the parts are mated, electrical contact between the connector and the electrode is made on the tapered surface of the upstanding contact member, and space 24 is provided between the upper surface of electrode plate 20 and the lower surface of connector 10.

Figure 2:
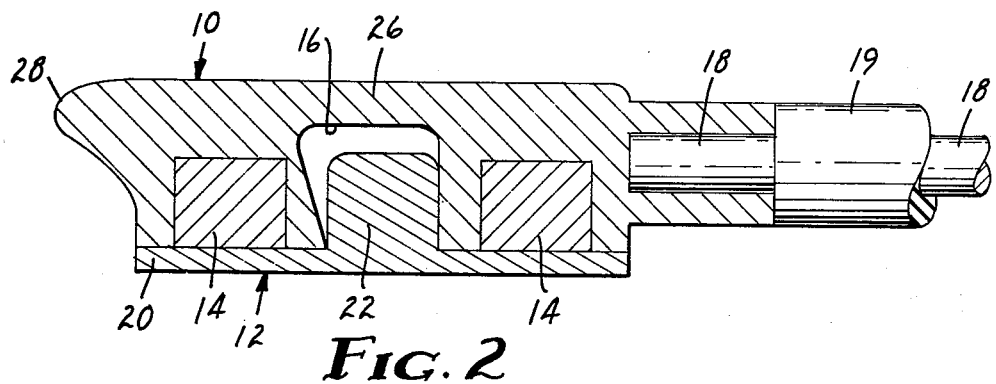
FIG. 2 is a sectional view of the connector and upper portion of the electrode illustrating the improved locking and disconnect features of the invention.

The assembly of FIG. 2 illustrates the improved locking and easy disconnect feature of the invention. In this embodiment, connection 10 comprises magnet 14 which is in the shape of a washer. The sides and upper surface of magnet 14 are surrounded by ferromagnetic shell 26. Ferromagnetic shell 26 surrounds the magnet in a cup-like fashion. "Cup" magnets of this type are well known in the art. The ferromagnetic cup causes the magnetic flux to be intensified at the edge of the magnet, thereby multiplying the holding force of the magnet. Cup magnets of this type are especially preferred for use in the connectors of the present invention because strong magnetic holding force can be achieved while keeping the size of the connector at a minimum.

The size of the magnet may vary depending upon the desired use of the electrode-connector assembly. In general, the magnet should provide a holding force of at least 250 grams, and, preferably, about 1000 grams. It has been found that a samarium cobalt magnet in the form of a washer 0.5 mm thick and 10 mm in diameter works well for most purposes. Using a magnet of this kind, a small, compact connector having a diameter of about twelve millimeters and a thickness of about 4 millimeters can be made.

Connector 10 has a hole 16 in the lower surface thereof for mating with the projecting portion of the electrode. Lead wire 18 is connected to one side of the connector and the opposite side of the connector has lifting means 28, illustrated as a projecting lip, for applying upward pressure with the thumb or finger to disconnect the connector from the electrode.

In the embodiment shown in FIG. 2, the upstanding contact member 22 is shown as a cylindrical member or pin firmly affixed to the electrode plate 20. This pin mates with hole 16 of the connector. Hole 16 is formed so that there is sufficient clearance between the wall of the hole and the pin to allow the connector to be tilted and lifted off the pin by applying upward force on lifting means 28. Clearance may be provided by outward tapering of the wall of hole 16 on the side adjacent to lifting means 28. It is obvious, however, that other configurations of the hole are possible to accomplish the same result. There is insufficient clearance between the pin and wall of the hole to allow the connector to be tilted and lifted off the pin by upward force on the lead wire. If the connector is tilted from the lead wire side, the pin will intercept the wall of the hole and prevent disconnection. This improvement prevents accidental disconnection by way of the lead wire, yet intentional disconnection is facilitated by way of the lifting means.

In FIG. 2, electrical contact between the connector and the electrode occurs on the surface of the electrode plate and no space is provided between the connector and the electrode plate. Although this embodiment is less preferred, it illustrates that the locking and easy disconnection feature can be practiced separately from the improved electrical contact feature shown in FIGS. 1, 3 and 6-8.

Figure 3:
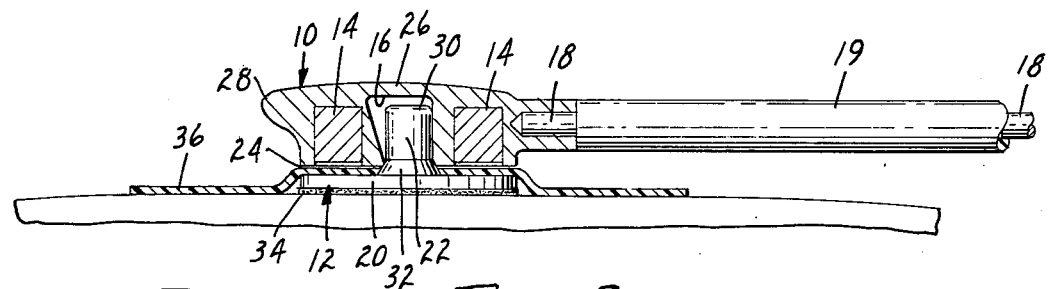
FIG. 3 is a sectional view of the preferred embodiment of the electrode-connector assembly on the skin of a patient.

FIG. 3 illustrates the preferred embodiment of the electrode-connector assembly of the invention containing both the improved electrical contact feature and the improved locking and easy disconnection feature.

Connector 10 comprises magnet 14 in the shape of a washer, the top and sides of which are surrounded by ferromagnetic shell 26 to form a cup magnet. Lead wire 18 is connected to one side of connector 10 and lifting means 28 extends from the opposite side of the connector from the lead wire. Connector 10 has a hole 16 in the lower surface thereof for mating with the projecting portion of the electrode.

Electrode 12 comprises electrode plate 20 of ferromagnetic material and an upstanding contact member or pin 22 firmly affixed thereto. Pin 22 has an elongated cylindrical body portion 30 and a beveled base portion 32. The diameter of mating hole 16 at its opening is less than the diameter of beveled base portion 32 of the pin. Consequently, when the connector and electrode are mated, the contact surface between the two is on the beveled base portion of the pin, and a space 24 is provided between the lower surface of the connector and the upper surface of electrode plate 22.

Hole 16 is formed so that when mated with pin 22, there is sufficient clearance between the pin and the wall of the hole to allow the connector to be tilted and lifted off the pin by applying upward force on lifting means 28. There is insufficient clearance between pin 22 and the wall of hole 16 to allow the connector to be tilted and lifted off the pin by applying upward force on the lead wire.

The lower surface of the electrode plate 20 is provided with electrical conducting means to conduct electrical impulses from the skin to the electrode plate. The electrical conductive means may consist of a porous pad containing conductive gel. Pregelled electrodes of this type are well known in the art. It is also well known in the art that pregelled electrodes are preferably packaged with a seal around the gel pad to keep the gel moist. Packaged pregelled electrodes are described in U.S. Pat. No. 3,805,769.

In FIG. 3, the electrical conducting means is illustrated as an electrically conductive pressure sensitive adhesive 34 such as that described in U.S. Pat. No. 3,911,906. The electrode is affixed to the skin by means of an adhesive strip 36 which is placed over the upper surface of the electrode plate 26 and partially fills the space between the connector and the electrode. Adhesive strip 36 extends outwardly beyond the perimeter of the electrode plate 26 so as to attach to the skin and hold the electrode firmly in place.

In operation, the electrode is placed on the skin of the patient which is generally prepared by cleaning and abrading. The electrical conductive material improves the electrical connection and reduces resistance between the skin and the electrode plate. The electrode is securely fastened to the skin by the adhesive strip. The connector is then connected to the electrode by mating with the upstanding contact member. The lead wire of the connector is connected to the monitoring device in the conventional manner.

Figure 4:
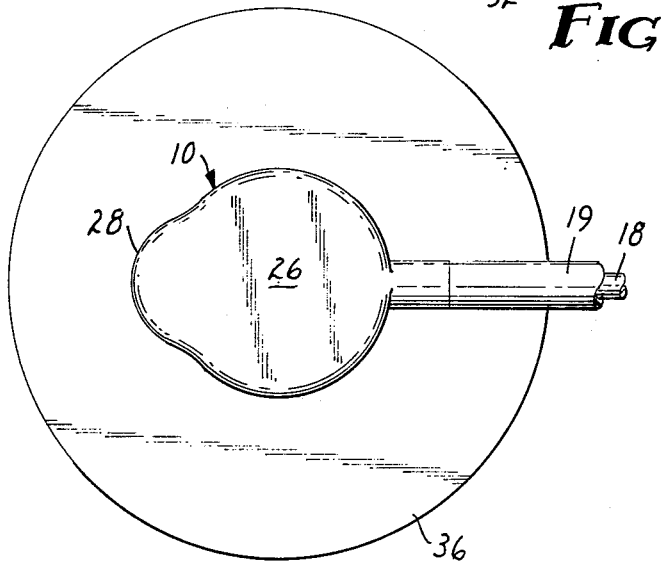
FIG. 4 is a plan view of the top of the connector-electrode assembly.

FIG. 4, shows a top view of the electrode-connector assembly of FIG. 3. The top of connector 10 shows ferromagnetic shell 26 with sheath 19 containing the lead wire 18 attached to one side and lifting means 28 extending outward from the opposite side. Adhesive strip 36, which secures the electrode to the skin, is seen extending from the periphery of the connector.

Figure 5:
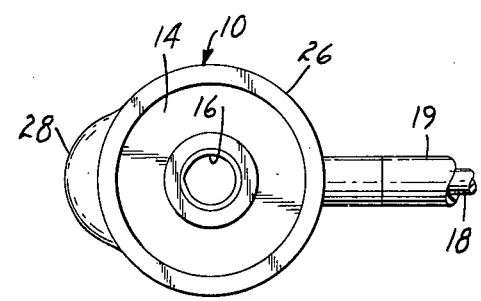
FIG. 5 is a plan view of the bottom of the connector portion of the assembly.

FIG. 5 is a bottom view of the connector showing ferromagnetic shell 26 and the magnet 14 therein. Hole 16 in the center of the connector mates with the upstanding contact member of the electrode. Sheath 19 containing lead wire 20 enters the connector on one side and lifting means 28 extends from the opposite side of the connector.

Figure 6:
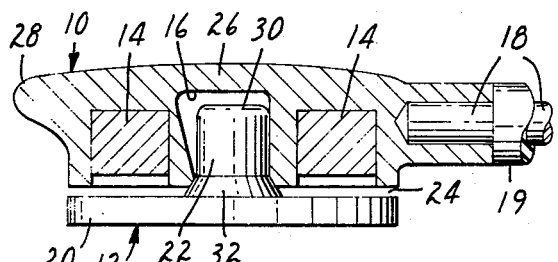
FIG. 6 is an enlarged sectional view of the connector and upper portion of electrode shown in FIG. 3.
Figure 7:
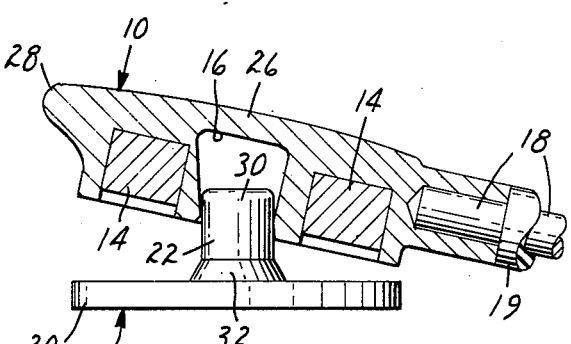
FIG. 7 is a sectional view of the connector and upper electrode showing the connector being disconnected from the electrode by use of the lifting means.
Figure 8:
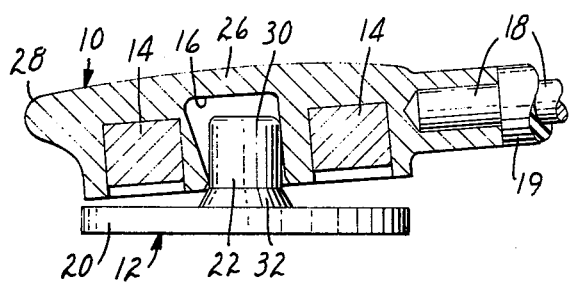
FIG. 8 is a sectional view of the connector and upper electrode showing the effect of applying upward tension to the lead wire.

FIG. 6 is an enlarged view of the connector and the upper portion of the electrode shown in FIG. 5. FIGS. 7 and 8 illustrate the effect of applying upward force on lifting means 28 and lead wire 18, respectively, when the connector and electrode are mated.

In FIG. 7, it is seen that by expanding the clearance or relief space between the pin 22 and the wall of hole 16 on the side adjacent to lifting means 28, the connector can be removed from the pin by applying upward force on lifting means 28. In this manner the magnetic force field holding the mating parts together can be broken at the edge, and considerably less force is required to disconnect the parts than if the connector is removed by straight axial pull across the entire force field.

In FIG. 8 it is seen that accidental disconnection of the mating parts by applying upward force on the lead wire is prevented by reducing the clearance or relief space between pin 22 and the wall of hole 16 on the side adjacent to the lead wire. Upward force on lead wire 18 causes pin 22 to intercept the wall of hole 16 and thereby interfere with further tilting and removal of the connector from the pin.

The electrode-connector of the present invention is especially suited for obtaining electrocardiograms and other biomedical monitoring such as electromyograms and electroencephalograms.

The electrode-connector assembly of the invention is easy to use and results in minimal discomfort to the patient. Connection of the mating parts is effortlessly made through the use of magnetic connecting means. Electrical contact between the parts is improved by concentrating the magnetic holding force over a small surface area. In addition, the chances of accidentally disconnecting the parts during monitoring is reduced by the locking features of the assembly, yet, intentional disconnection at the end of the monitoring period is facilitated by the special disconnect feature.

What is claimed is:
1. An electrode-connector assembly comprising: an electrode comprising:
   (1) a ferromagnetic electrode plate having an upper surface and a lower surface;
   (2) an upstanding electrically conductive contact member firmly affixed to the upper surface of said electrode plate adapted to mate with the connector portion of said assembly;
   (3) means for affixing the electrode plate to the surface of the skin with said contact member projecting away from the skin; and
   (4) means for conducting electrical impulses between the skin and the electrode plate;
and a connector electrically and mechanically mated to said electrode, comprising:
   (1) a magnet having an upper surface and a lower surface and side walls with a hole in said lower surface into which said upstanding contact member is releasably fitted so that said contact member electrically contacts said connector on some portion of said contact member and a space exists between said magnet and the upper surface of said electrode plate; and (2) a lead wire electrically connected to said magnet.

2. The electrode-connector assembly according to claim 1 wherein said contact member further comprises an elongated cylindrical body portion and a beveled base portion affixed to the upper surface of said electrode plate, said beveled base portion providing the electrical contact portion between said connector and said contact member; and wherein the diameter of said hole is larger than the diameter of said cylindrical portion and smaller than the diameter of said beveled base portion so that said connector contacts said beveled base portion.

3. The electrode-connector assembly according to claim 2 wherein the connector further comprises a ferromagnetic shell surrounding the side walls and upper surface of said magnet forming a cup magnet.

4. The electrode-connector according to claim 3 wherein the connector further comprises lifting means on said cup magnet to which mechanical force may be applied to disconnect said connector from said electrode, said lifting means being located on the side of said cup magnet opposite from the attachment of said lead wire and wherein a clearance is provided between said upstanding contact member and the wall of said hole on the side adjacent to said lifting means such that upward force on said lead wire causes the wall of said hole to intercept said upstanding contact member thereby preventing disconnection of said connector from said electrode, and upward force on said lifting means does not cause the wall of said hole to intercept said contact member thereby allowing disconnection of said connector from said electrode.

5. An electrode-connector assembly comprising: an electrode comprising:

(1) a ferromagnetic electrode plate having an upper surface and a lower surface;

(2) an upstanding elongated electrically-conductive contact member firmly affixed to the upper surface of said electrode plate adapted to mate with the connector portion of said assembly;

(3) means for affixing said electrode plate to the surface of the skin with said contact member projecting away from the skin; and (4) means for conducting electrical impulses between the skin and the electrode plate; and a connector electrically and mechanically mated to said electrode comprising:

(1) a magnet having an upper surface and a lower surface with a hole in said lower surface into which said contact member is releasably fitted so that said contact member electrically contacts said magnet on some portion of said contact member;

(2) a lead wire electrically connected to said magnet;

(3) lifting means on said magnet to which mechanical force may be applied to disconnect said connector from said electrode, said lifting means being on the side of said magnet opposite the attachment of said lead wire; and (4) wherein a clearance is provided between said upstanding contact member and the wall of said hole on the side adjacent to said lifting means such that upward force on said lead wire causes the wall of said hole to intercept said contact member thereby preventing disconnection of said connector from said electrode and upward force on said lifting means will not cause the wall of said hole to intercept said contact member and allows disconnection of said connector from said electrode.

6. An electrode comprising:

a ferromagnetic electrode plate having an upper surface and a lower surface; an upstanding electrically-conductive contact member firmly affixed to the upper surface of said electrode plate having an elongated cylindrical body portion and an outwardly beveled base portion, said beveled base portion affixed to the upper surface of said electrode plate, and said base portion providing an electrical contact surface;

means for affixing the electrode plate to the surface of the skin with said contact member projecting away from the skin; and means for conducting electrical impulses between the skin and the electrode plate.

7. A connector for mating with an electrode and transmitting electrical impulses therefrom comprising:

a magnet having an upper surface and a lower surface and side walls;

a ferromagnetic shell surrounding said side walls and upper surface of said magnet forming a cup magnet;

a lead wire electrically connected to said ferromagnetic shell; and lifting means on said cup magnet to which mechanical force may be applied to disconnect said connector from the electrode, said lifting means being located on the side of said cup magnet opposite the attachment of the lead wire; said cup magnet having a hole in the lower surface thereof for mating with the male portion of the electrode, said hole being formed so that when mated there is sufficient clearance between the wall of said hole and the male portion of the electrode on the side adjacent to said lifting means to lift off the connector from the male portion of the electrode by upward force on the lifting means, and clearance between the wall of the hole and the male portion of the electrode is such that upward force on the lead wire causes the wall of the hole to intercept the male portion of the electrode thereby preventing disconnection by upward force on said lead wire.

* * * * *